US011033230B2

(12) United States Patent
Funane et al.

(10) Patent No.: US 11,033,230 B2
(45) Date of Patent: Jun. 15, 2021

(54) PROBE HOLDER MODULE AND METHOD FOR CONFIGURING PROBE HOLDER USING SAME

(71) Applicant: Hitachi, Ltd., Tokyo (JP)

(72) Inventors: Tsukasa Funane, Tokyo (JP); Masashi Kiguchi, Tokyo (JP); Hiroki Sato, Tokyo (JP)

(73) Assignee: Hitachi, Ltd., Tokyo (JP)

(*) Notice: Subject to any disclaimer, the term of this patent is extended or adjusted under 35 U.S.C. 154(b) by 757 days.

(21) Appl. No.: 15/580,024

(22) PCT Filed: Jun. 19, 2015

(86) PCT No.: PCT/JP2015/067793
§ 371 (c)(1),
(2) Date: Dec. 6, 2017

(87) PCT Pub. No.: WO2016/203656
PCT Pub. Date: Dec. 22, 2016

(65) Prior Publication Data
US 2018/0153472 A1    Jun. 7, 2018

(51) Int. Cl.
*A61B 5/00* (2006.01)
*A61B 5/1455* (2006.01)

(52) U.S. Cl.
CPC .......... *A61B 5/6835* (2013.01); *A61B 5/0042* (2013.01); *A61B 5/14553* (2013.01); *A61B 5/6814* (2013.01)

(58) Field of Classification Search
CPC . A61B 5/6814; A61B 5/0042; A61B 5/14553; A61B 2562/04; A61B 2562/16; A61B 2562/225
See application file for complete search history.

(56) References Cited

U.S. PATENT DOCUMENTS 4,967,038 A * 10/1990 Gevins ................. A61B 5/0017
600/383
2006/0058594 A1    3/2006 Ishizuka et al.
(Continued)

FOREIGN PATENT DOCUMENTS

JP          9-28696 A        2/1997
JP     2004-205493 A        7/2004
(Continued)

OTHER PUBLICATIONS

International Search Report (PCT/ISA/210) issued in PCT Application No. PCT/JP2015/067793 dated Sep. 1, 2015 with English translation (3 pages).
(Continued)

*Primary Examiner* — Rajeev P Siripurapu
(74) *Attorney, Agent, or Firm* — Crowell & Moring LLP

(57) ABSTRACT

There is disclosed a probe holder module that configures a part of a probe holder for an optical measurement which holds a light emission probe and a light detection probe and can be mounted on an object to be measured and configures the probe holder for optical measurement by combining a plurality of probe holder modules, the probe holder module including a holding part for mechanically holding at least one of the light emission probe and the light detection probe, at least one of an electric circuit and electric wiring to be electrically connected to at least one of the light emission probe and the light detection probe, a terminal for connecting at least one of the light emission probe and the light detection probe and at least one of the electric circuit and the electric wiring, a mechanical connection part to be mechanically connecting other probe holder module, and an electrical connection part to be electrically connected to the other probe holder module.

15 Claims, 17 Drawing Sheets

(56) References Cited

U.S. PATENT DOCUMENTS

2013/0116521 A1* 5/2013 Inoue .................. G01N 21/474
                                                        600/328
2017/0319072 A1* 11/2017 Bae ......................... A61B 6/00

FOREIGN PATENT DOCUMENTS

| JP | 2006-305334 A | 11/2006 |
| JP | 2013-13547 A | 1/2013 |

OTHER PUBLICATIONS

Japanese-language Written Opinion (PCT/ISA/237) issued in PCT Application No. PCT/JP2015/067793 dated Sep. 1, 2015 (3 pages).
Maki et al., "Spatial and Temporal Analysis of Human Motor Activity Using Noninvasive NIR Topography", Medical Physics, Dec. 1995, pp. 1997-2005, vol. 22, No. 12.

* cited by examiner

[Fig. 1]
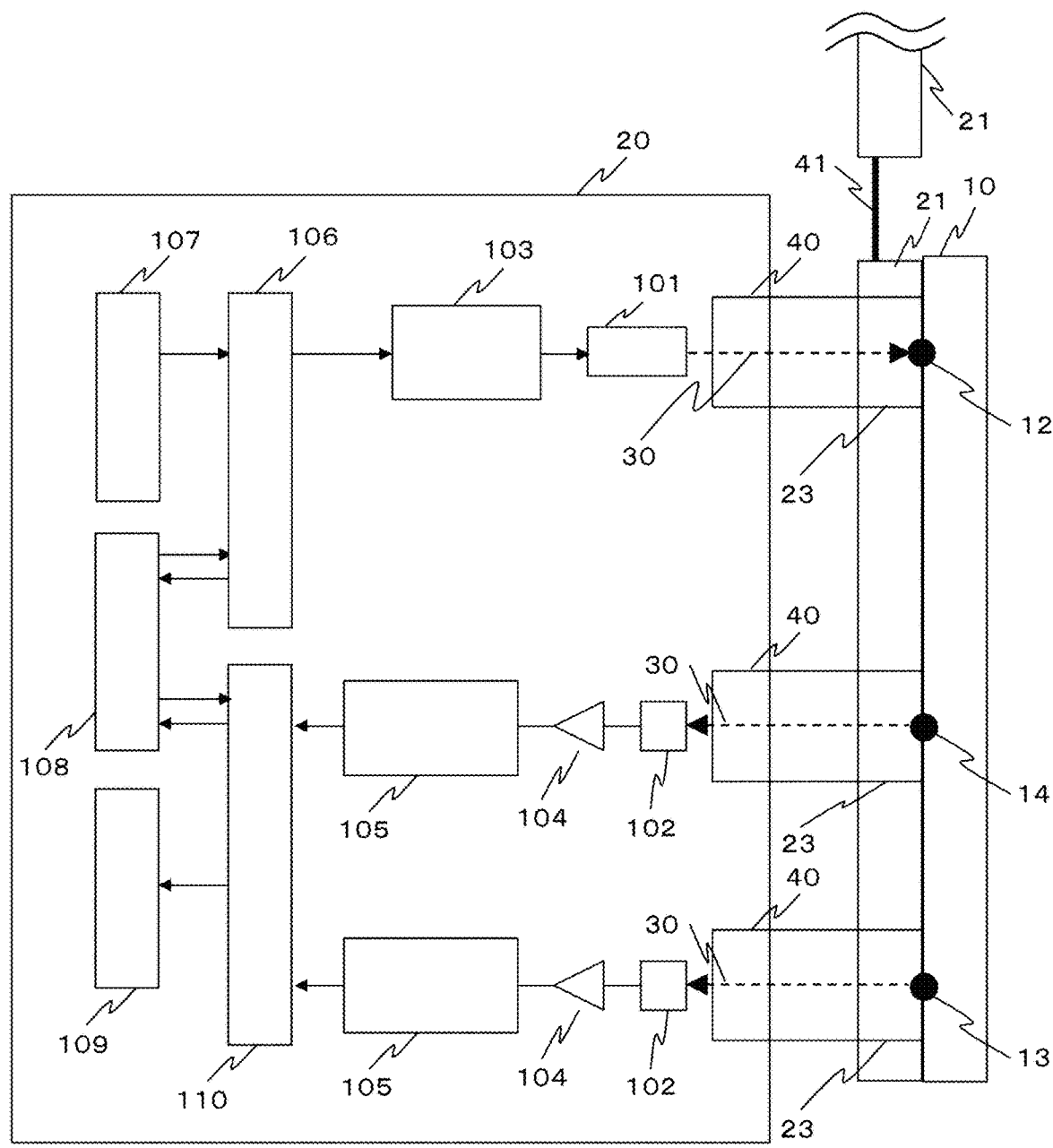

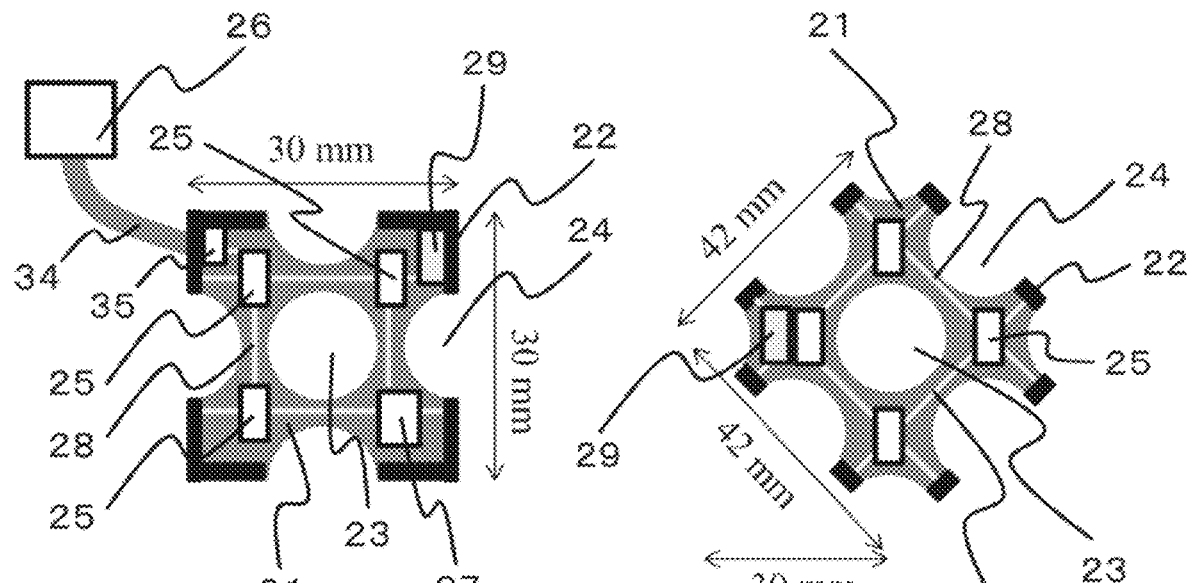
FIG. 2A  FIG. 2B
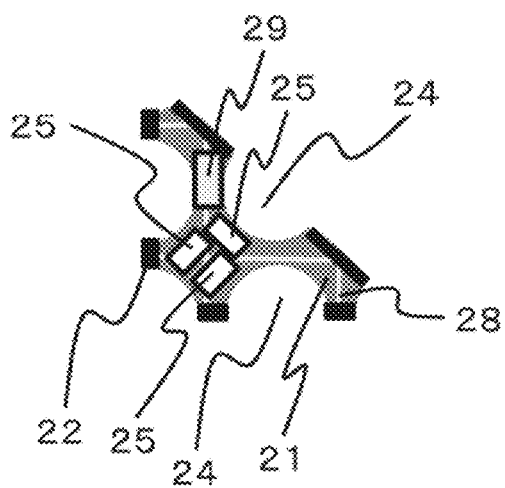  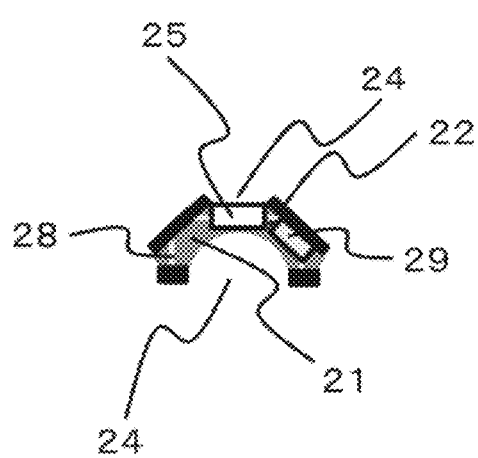
FIG. 2C  FIG. 2D

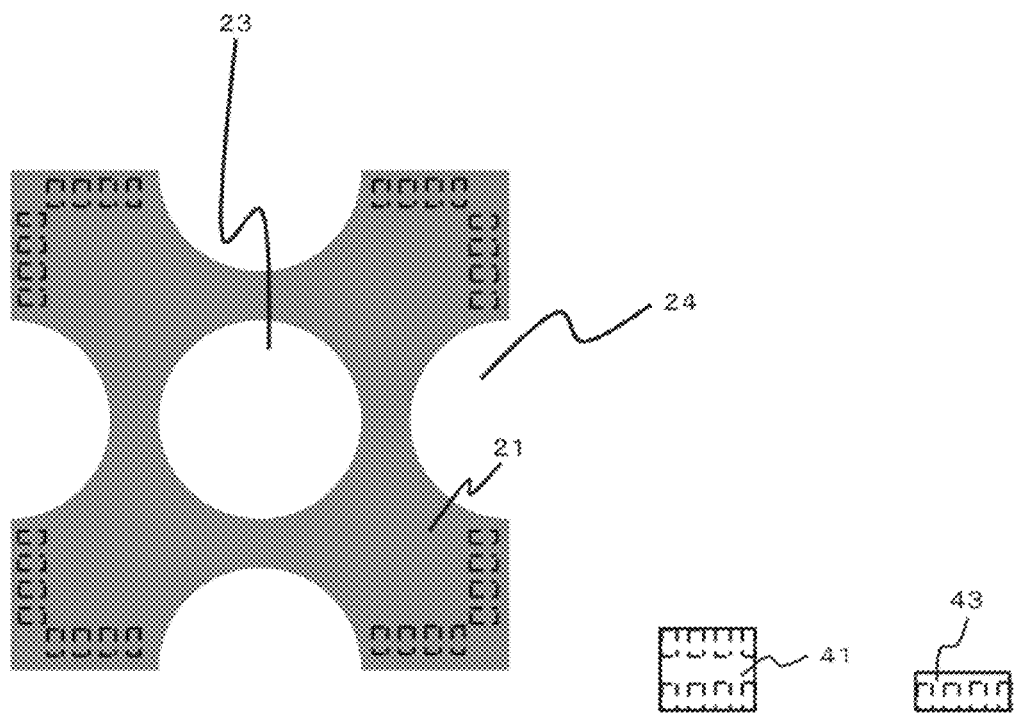
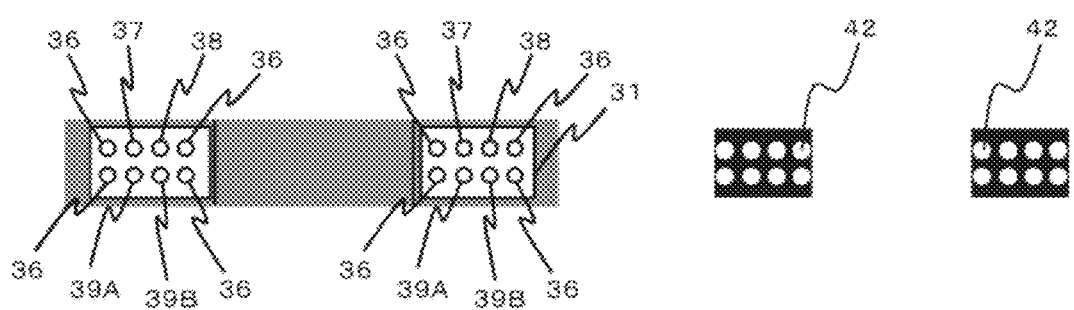
FIG. 6A    FIG. 6B    FIG. 6C

[Fig. 7]
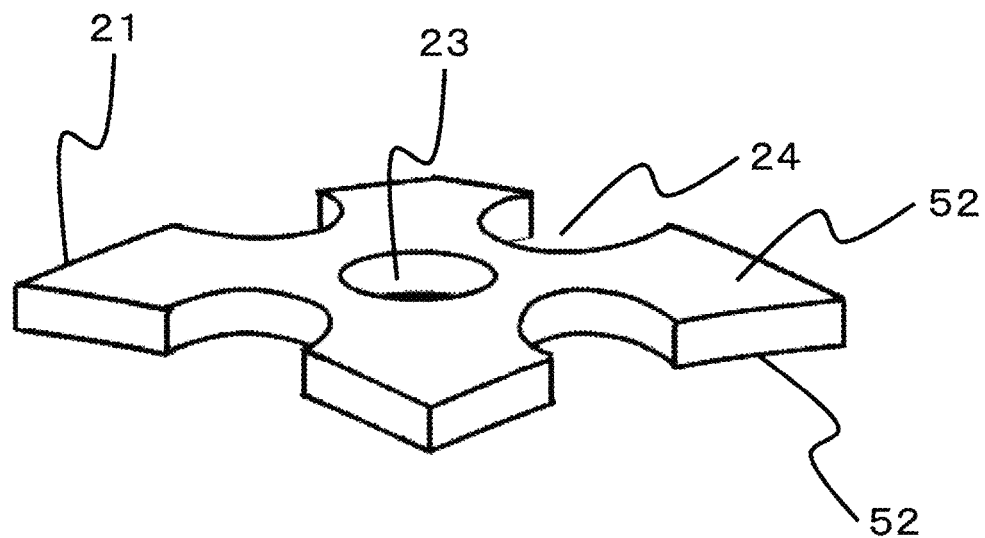
[Fig. 8]
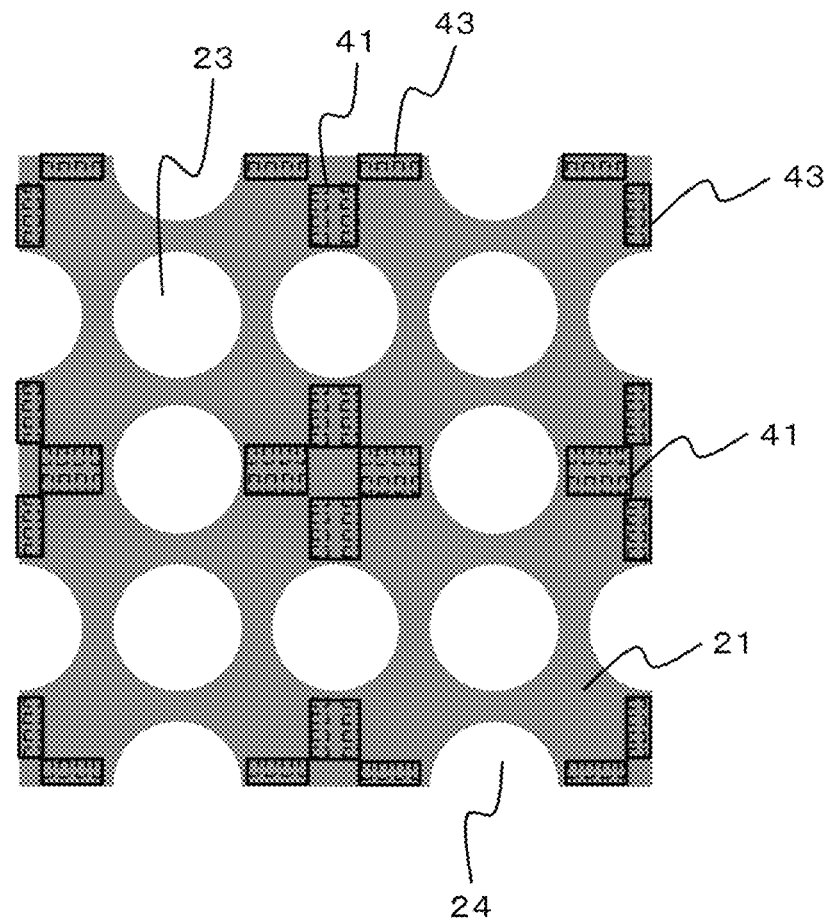

[Fig. 11]
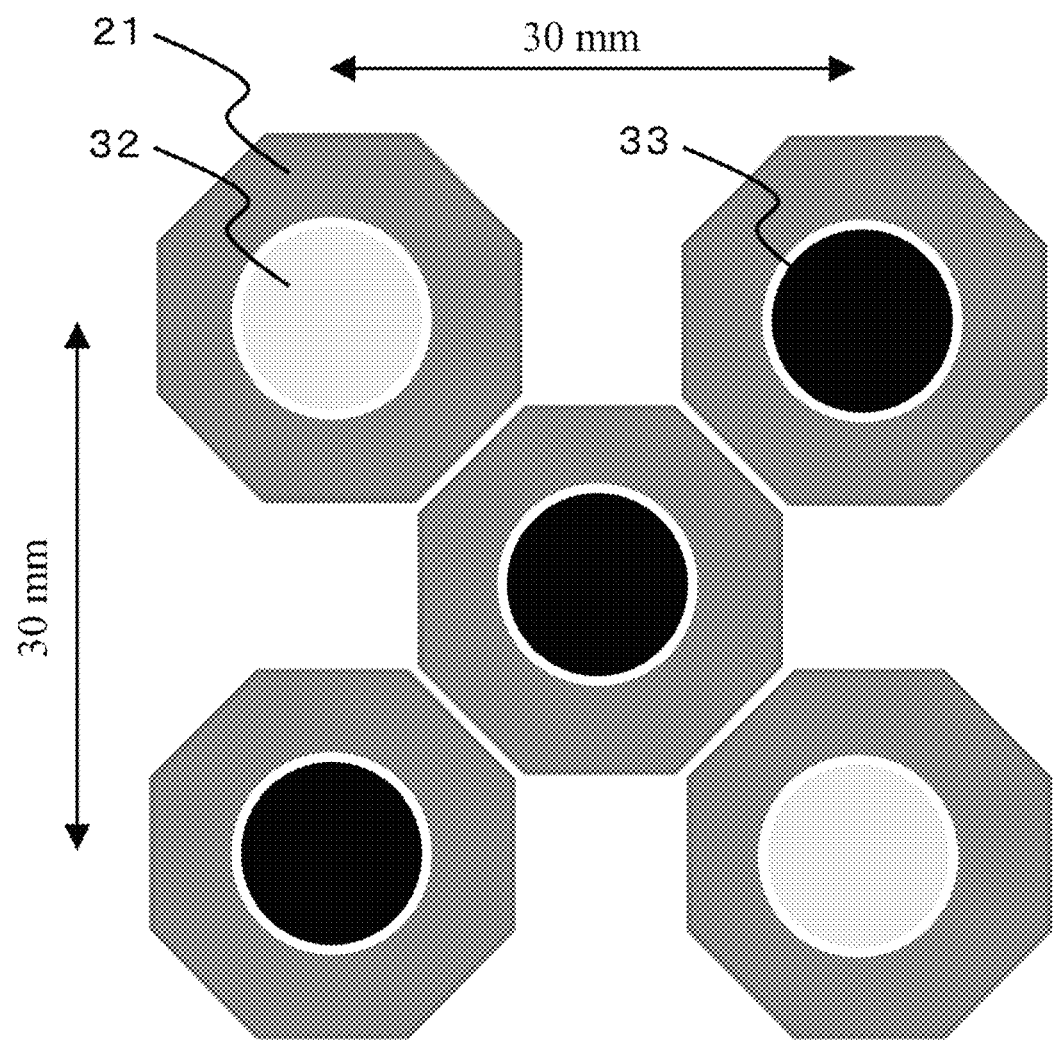

[Fig. 12]
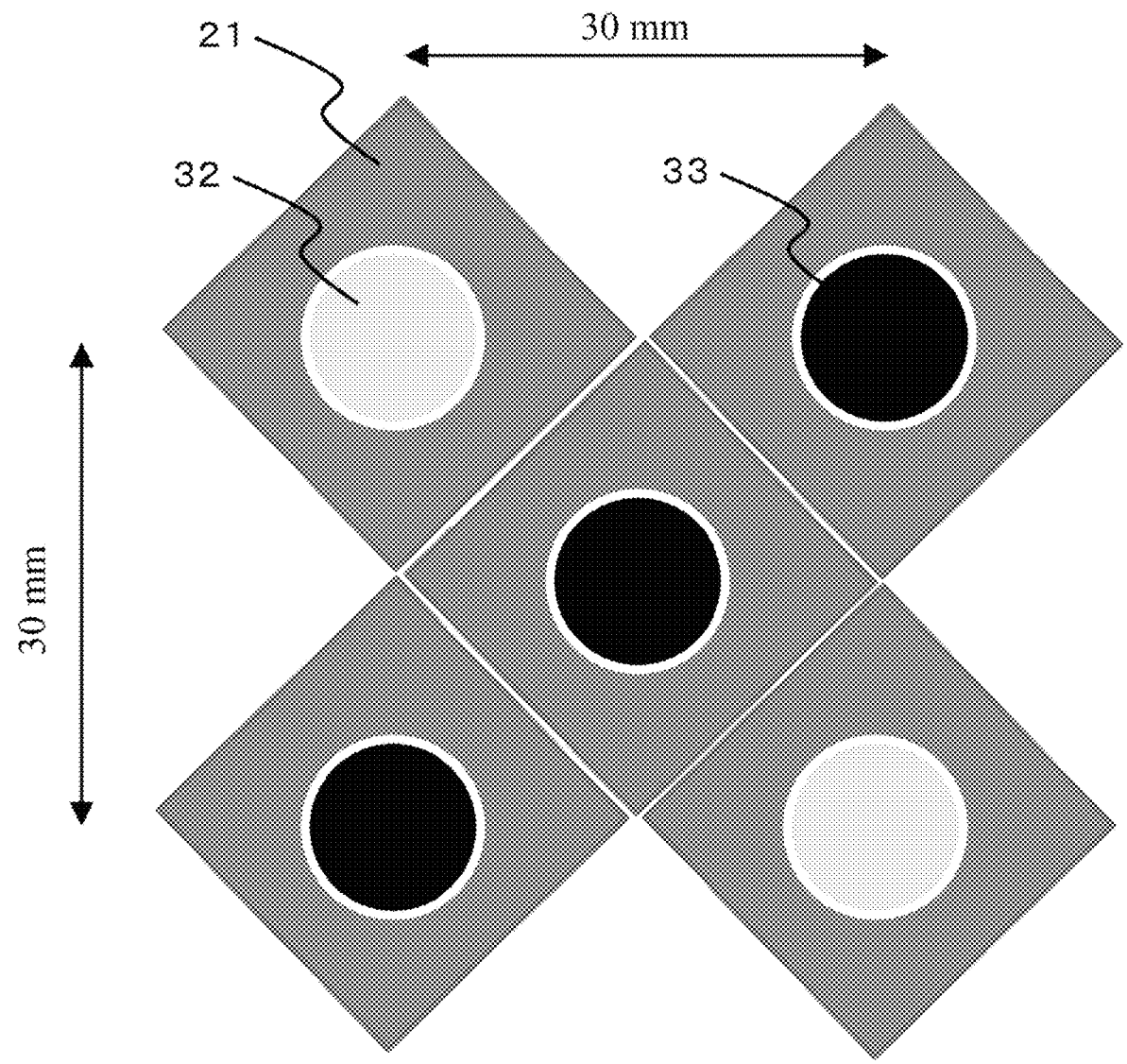

[Fig. 13]
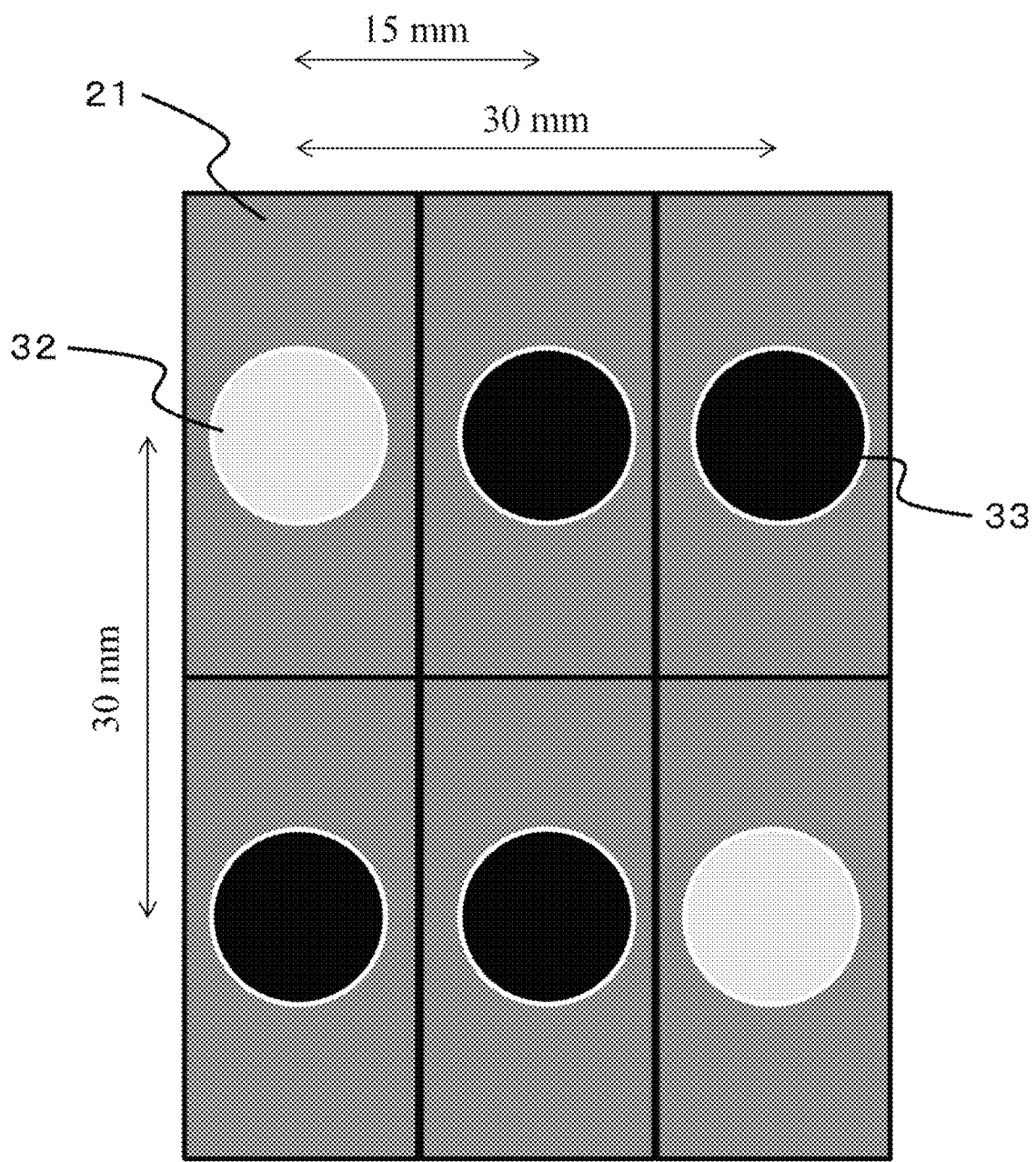

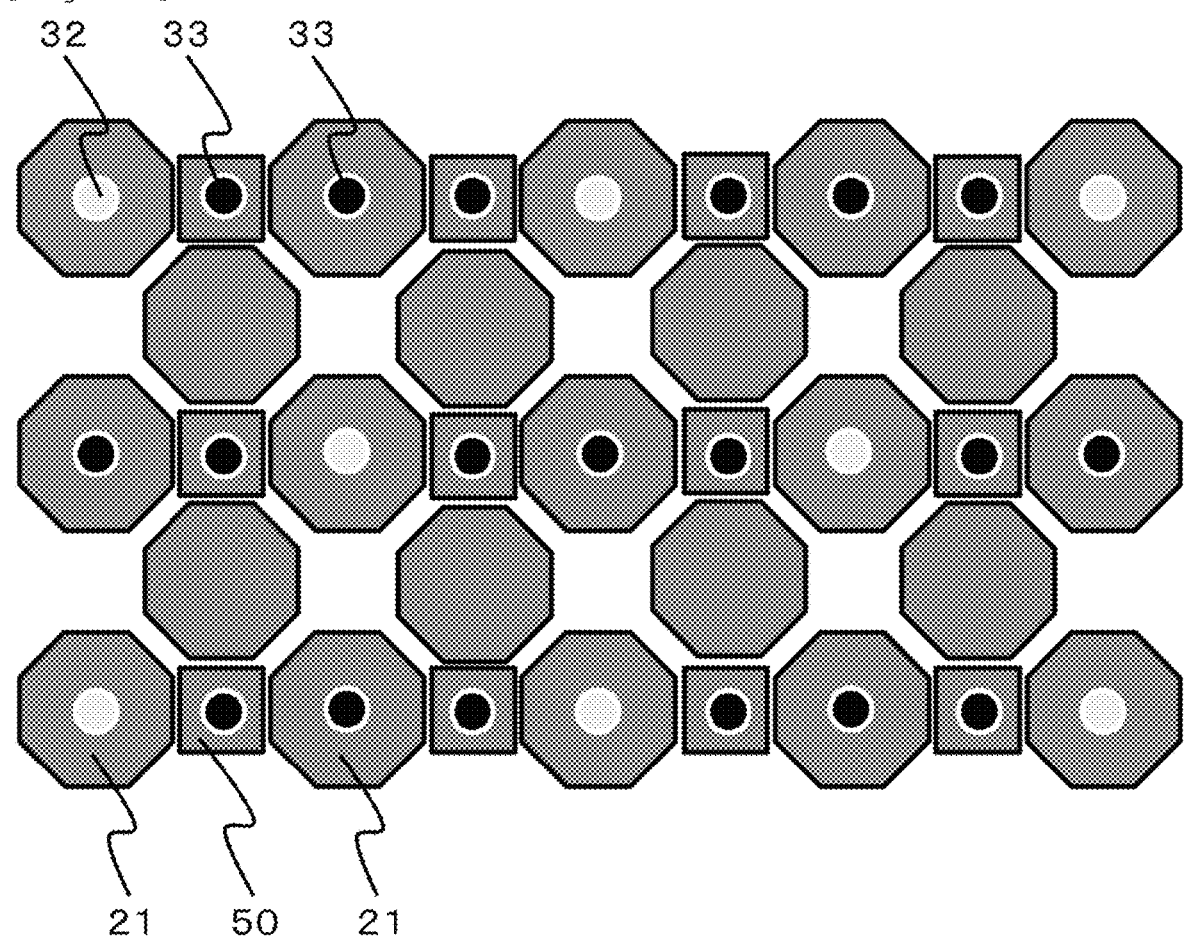
[Fig. 14]

[Fig. 15]
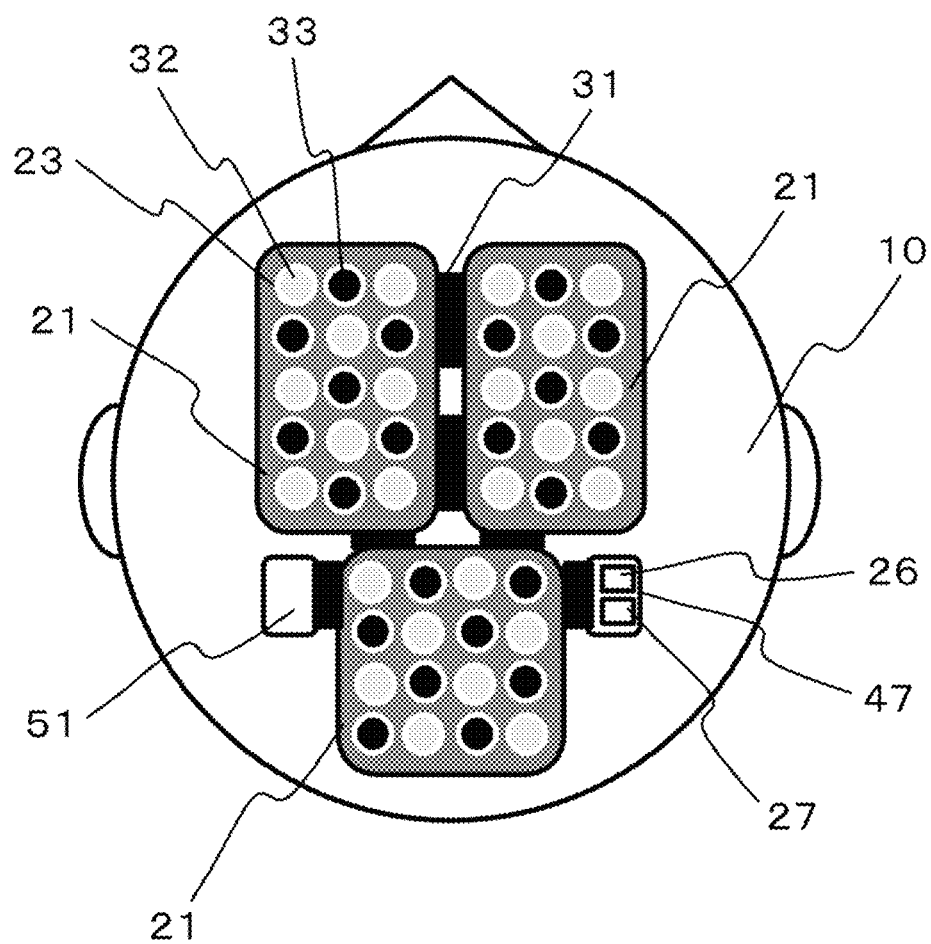

[Fig. 16]
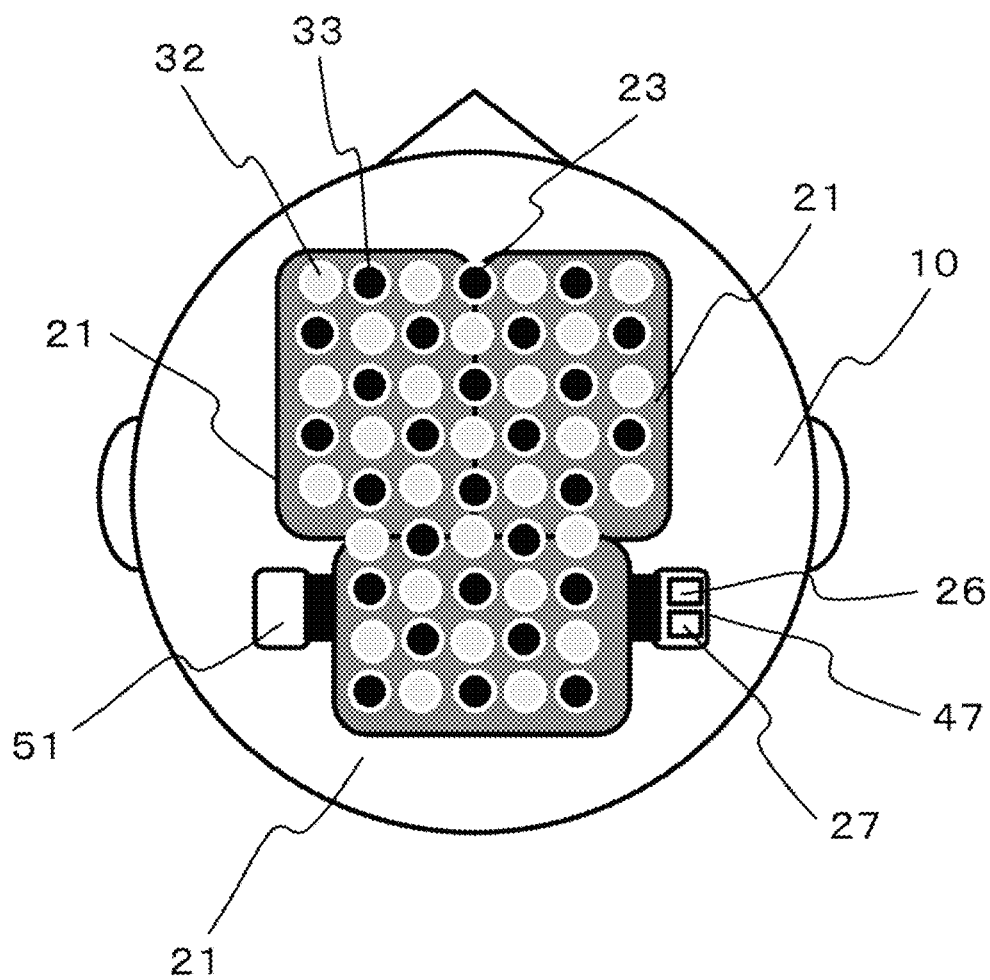

[Fig. 17]
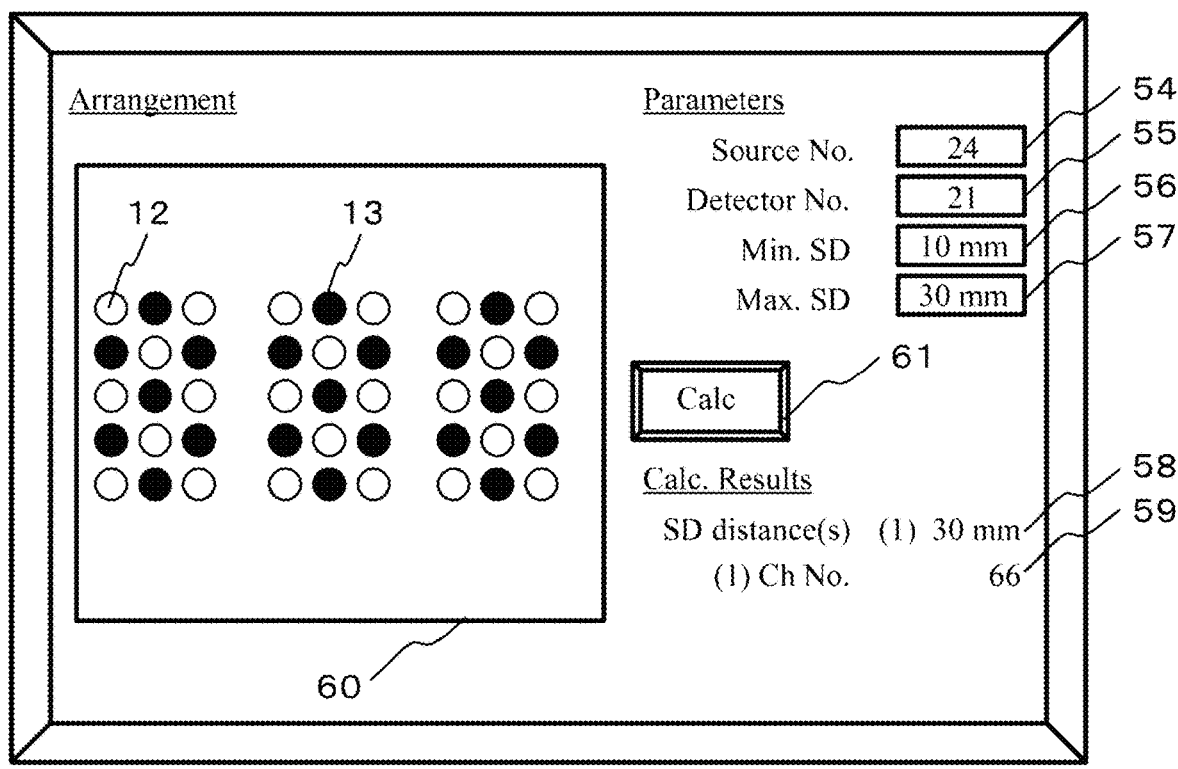

[Fig. 18]
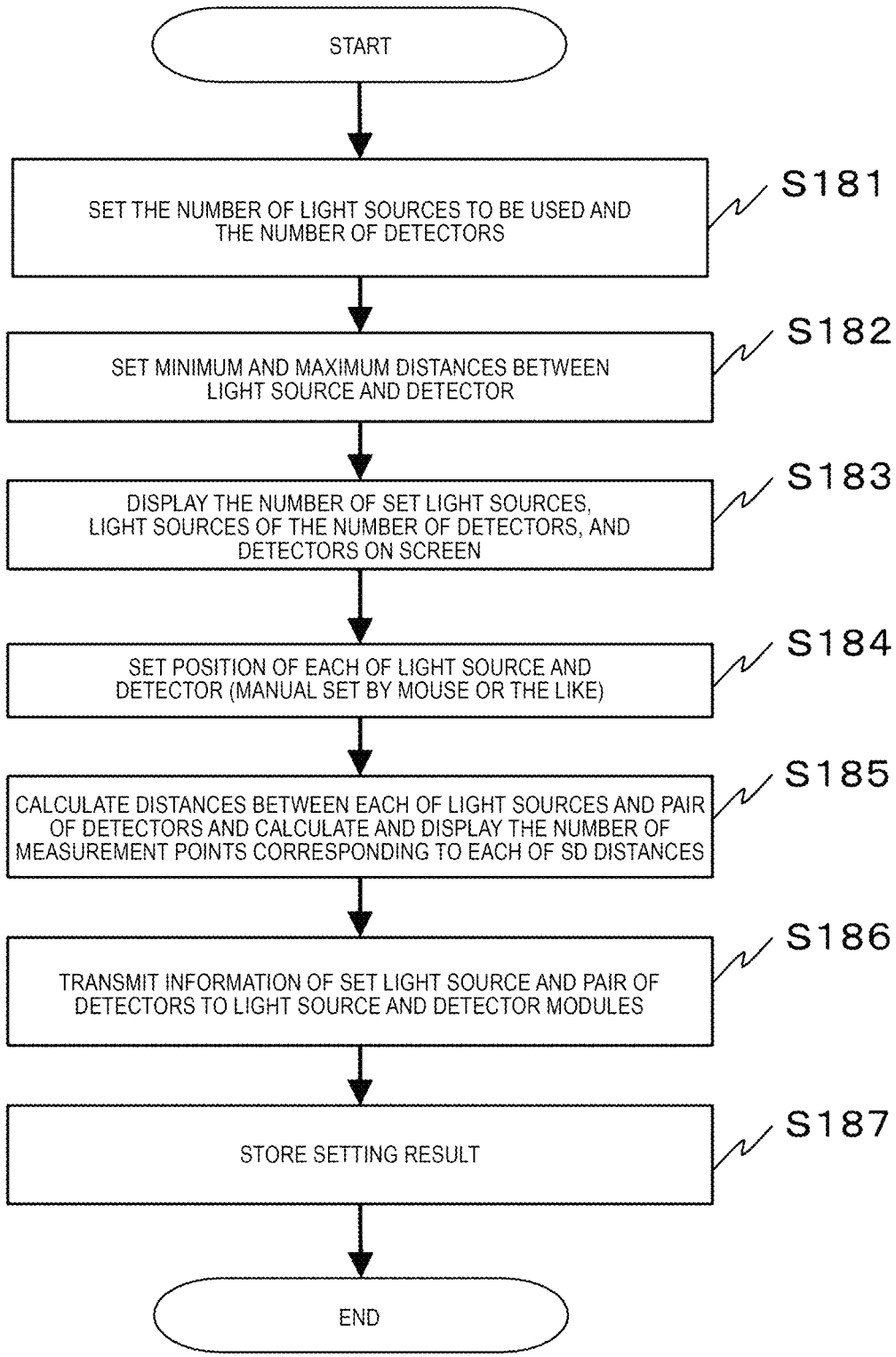

PROBE HOLDER MODULE AND METHOD FOR CONFIGURING PROBE HOLDER USING SAME

TECHNICAL FIELD

The present invention relates to an optical measurement device using light, particularly visible light or near-infrared light. In particular, the present invention relates to a technology for measuring in-vivo information such as cerebral hemodynamic changes accompanying cerebral activity.

BACKGROUND ART

A brain function measurement device using near-infrared spectroscopy (NIRS) can be used as medical and research equipment, or can be used for confirming an effect of education and rehabilitation, for health management at home, and a market survey such as a product monitor. In addition, the device can be used for tissue oxygen saturation measurement and muscle oxygen metabolism measurement by the same method. Furthermore, the device can be used for a general absorption spectroscopy device in which a light scattering body is to be measured including measurement of sugar concentration of fruit.

In such a technology, in order to obtain a probe arrangement for measuring the necessary number of measurement points depending on a purpose, a light source and detector arrangement are configured by preparing various kinds of probe holders so far.

PTL 1 discloses an optical measurement device that includes a probe holder in which a circuit is built, does not need to perform calibration again even in a case where a probe is replaced, and can perform measurement under optimum conditions. However, there is no disclosure of a method for extending the probe holder in a state where electrical coupling is maintained without excess or deficiency by as much as necessary.

CITATION LIST

Patent Literature

PTL 1: JP-A-2013-13547

Non-Patent Literature

NPL 1: A. Maki et al., "Spatial and temporal analysis of human motor activity using noninvasive NIR topography, "Medical Physics, Vol. 22, No. 12, pp. 1997 to 2005 (1995)

SUMMARY OF INVENTION

Technical Problem

The present inventors examined modularizing the light source and the detector in order to extend the probe holder of the optical measurement device without excess or deficiency by as much as necessary.

Here, instead of modularizing a light sources and a detector and controlling all the light sources and all the detectors in a device main body, in the configuration in which each light source and detector module includes a control unit, an electric circuit such as a communication line inside the probe holder is required for communication and control between the modules.

However, there is no disclosure of a specific proposal of the probe holder in which an electric circuit is built and which has a module configuration capable of stably performing replacement of the probe holder or continuous probe extension so far.

An object of the present invention is to easily and stably change and expand the probe arrangement in the optical measurement device.

Solution to Problem

An aspect of the present invention for solving the problem of the present invention is a probe holder module that configures a part of a probe holder for an optical measurement which holds a light emission probe and a light detection probe and can be mounted on an object to be measured and configures the probe holder for optical measurement by combining a plurality of probe holder module. The probe holder module includes a holding part for mechanically holding at least one of the light emission probe and the light detection probe, at least one of an electric circuit and electric wiring to be electrically connected to at least one of the light emission probe and the light detection probe, a terminal for connecting at least one of the light emission probe and the light detection probe and at least one of the electric circuit and the electric wiring, a mechanical connection part to be mechanically connecting other probe holder module, and an electrical connection part to be electrically connected to the other probe holder module.

In a further preferred embodiment, the holding part mechanically holds at least one of the light emission probe and the light detection probe in cooperation with a holding part of the other probe holder module.

Another aspect of the present invention is a biological optical measurement probe holder module including a connector electrically connectable to at least one of a light emission probe and a light detection probe and at least one of an electric circuit and electric wiring. The module includes a joint part that is joined to other biological optical measurement probe holder module and an electrical connection part that is electrically connected to the other biological optical measurement probe holder module.

In a further preferred embodiment, a probe insertion hole side surface that substantially coincides with a part of a side surface shape of at least one of the light emission probe and the light detection probe is provided.

The other aspect of the present invention is a method for configuring a probe holder which configures an optical measurement probe holder by coupling with a plurality of probe holder modules. In the method, a plurality of probe holder modules including a holding part for mechanically holding at least one of the light emission probe and the light detection probe, at least one of an electric circuit and electric wiring to be electrically connected to at least one of the light emission probe and the light detection probe, a terminal for connecting at least one of the light emission probe and the light detection probe and at least one of the electric circuit and the electric wiring, a mechanical connection part to be mechanically connecting other probe holder module, and an electrical connection part to be electrically connected to the other probe holder module is prepared as the probe holder module. The probe holder is coupling with the other probe holder module by the mechanical connection part and the electrical connection part to configure an optical measurement probe holder.

In a further preferred embodiment, the holding part of the probe holder module forms a part of an insertion hole where a part of a side surface of the probe holder module inserts at least one of the light emission probe and the light detection probe. The holding part mechanically holds at least one of the light emission probe and the light detection probe in cooperation with a part of the insertion hole and the other probe holder module.

Advantageous Effects of Invention

According to the present invention, a stable and easy extension of the probe holder and the free probe arrangement in the optical measurement device can be obtained.

BRIEF DESCRIPTION OF DRAWINGS

FIG. 1 is a block diagram illustrating an example of a device configuration of an example.

FIGS. 2A to 2D are plan views of a probe holder module having an inter-holder electrical connection connector.

FIGS. 6A to 6C illustrate details of an electric connection terminal built-in joint part, and a plan view and a side view of a probe holder module and an inter-probe holder relay connector.

FIG. 7 is a perspective view of the probe holder module having a curved surface.

FIG. 8 is a plan view illustrating the probe holder configured by combining the probe holder module, the inter-probe holder relay connector, and a terminal cover.

FIG. 11 is a plan view illustrating a substantially regular octagonal probe holder module.

FIG. 12 is a plan view illustrating a substantially square probe holder module.

FIG. 13 is a plan view illustrating a substantially rectangular probe holder module.

FIG. 14 is a plan view illustrating a combined arrangement of the substantially regular octagonal probe holder module and the substantially square probe holder module.

FIG. 15 is a plan view illustrating an example in which the probe holder module is arranged on a human head.

FIG. 16 is a plan view illustrating an example in which the probe holder module is arranged on the human head so as to form a probe insertion hole.

FIG. 17 is a plan view of a probe arrangement design screen.

FIG. 18 is a flow chart when setting the probe arrangement.

DESCRIPTION OF EMBODIMENTS

Figure 3A:
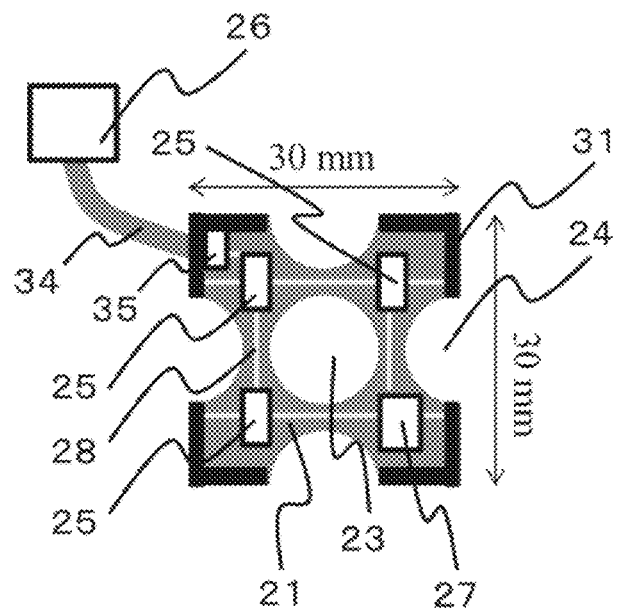
FIGS. 3A to 3D are plan views of the probe holder module in which the inter-holder electrical connection connector is built in a joint part.

The following describes in detail embodiments with reference to the drawings. However, the present invention should not be construed as being limited to the description in the following embodiments. It can be easily understood by a person skilled in the art that the specific configuration can be altered unless the spirits and purpose of the present invention are deviated.

Note that in structures of the present invention described below, the same portions or portions having similar functions are denoted by the same reference numerals in different drawings, and description thereof is not repeated in some cases.

Notations such as "first", "second", "third", or the like in the present specification or the like are given to identify constituent elements, and do not necessarily limit the number or order. In addition, reference numeral for identifying the constituent element is used for each context, and the reference numeral used in one context does not necessarily indicate the same configuration in other contexts. In addition, it does not preclude that the constituent element identified by a certain reference numeral overlaps as the function of the constituent element identified by the other reference numeral.

The positions, sizes, shapes, ranges, and the like of the respective configurations illustrated in drawings and the like may not show actual positions, sizes, shapes, ranges, and the like in order to facilitate understanding of the invention. Accordingly, the present invention is not necessarily limited to the positions, sizes, shapes, ranges, and the like disclosed in the drawings and the like.

Publications, patents, and patent applications cited in the present specification configure a part of the description of the present specification as such.

A constituent element expressed in a singular form in the present specification should be understood as the concept of including a plurality of those constituent elements as long as it explicitly means only a single constituent element in the context.

In the following examples, a detailed description of a configuration for obtaining a probe holder that can be easily arranged freely by a module formed of probe holder parts built in an electric circuit will be given. In the examples, there is disclosed an example in which an inter-module joint part is provided and continuous probe holder expansion is obtained by providing a probe insertion hole side surface for forming a probe insertion hole after joining. By providing an electrical connection part that enables electrical coupling between each of probe holder modules, communication between the probes or communication with the control module is enabled. The electrical connection part may be built in the inter-module joint part. Modular light sources and detectors are replaceable at the time of failure and are easy to maintain. By allowing the probe holder to extend, expansion of the number of probes becomes also easy. A tile type probe holder capable of being electrically connected to each other is configured so that an arbitrary probe arrangement can be created in an expandable manner.

The probe is extensible by the joint part between typical probe arrangement (3×3, 4×4, and 3×5). A configuration for obtaining automatic detection on power and a selection method of a detection system depending on the probe arrangement by a graphical user interface (GUI) for arrangement design is disclosed.

A representative configuration described in detail in the examples will be described below.

There is disclosed a biological optical measurement probe holder module including a connector that can be electrically connected to a light emission probe or a light detection probe, an electric circuit, an electrical connection part that is electrically connected to other biological optical measurement probe holder module, and a joint part that is joined to the other biological optical measurement probe holder module.

The biological optical measurement probe holder module having a probe insertion hole side surface that substantially coincides with a side surface shape of the light emission probe or the light detection probe is disclosed.

The biological optical measurement probe holder module in which the electrical connection part is built in the connection part is disclosed.

The biological optical measurement probe holder module the electrical connection part which includes at least a signal line, a clock line, and a power supply line is disclosed.

The biological optical measurement probe holder module capable of varying an SD distance which is the distance between a light emitter and a detector is disclosed.

The biological optical measurement probe holder module in which the distance between biological optical measurement probe holder modules to be connected and a connection angle can be adjusted is disclosed.

The biological optical measurement probe holder module having a curved surface on a contact surface to a human head is disclosed.

The biological optical measurement probe holder module having a function of switching the light emission probe or the light detection probe as a probe to be inserted is disclosed.

The biological optical measurement probe holder module including a probe holder module dedicated for short SD distance is disclosed.

The biological optical measurement probe holder module including a probe holder module which is dedicated for connection and in which neither the light emission probe nor the light detection probe is connected is disclosed.

FIG. 1 illustrates overall configuration of a device in the present examples. It is a configuration example of a biological optical measurement device that irradiates a living body with light, and detects light which is scattered and absorbed in the living body and propagated.

Light 30 radiated from one or a plurality of light sources 101 included in a main body of a device 20 is allowed to enter a subject 10 via an optical waveguide 40. The optical waveguide 40 is to be inserted into and fixed on a probe insertion hole 23 of a probe holder module 21. The light 30 enters inside the subject 10 from a light emission position 12, penetrates inside the subject 10, and propagates, and then is detected by separate light detectors 102 from light detection positions 13 and 14 located away from the light emission position 12 via the optical waveguide 40.

A distance between the light emission position 12 and the light detection position 13 is defined as $d_1$ and a distance between the light emission position 12 and the light detection position 14 is defined as $d_2$. A case where there is two light detection positions is illustrated in here. However, three or more light detection positions may be provided.

Here, one or a plurality of the light sources 101 is a semiconductor laser (LD), a light emitting diode (LED), or the like, and one or a plurality of the light detectors 102 may be an avalanche photodiode (APD), a photodiode (PD), a photomultiplier tube (PMT), or the like. In addition, the optical waveguide 40 may be an optical fiber, glass, a light guide, or the like.

The light source 101 is driven by a light source driving device 103. One or a plurality of light detector outputs are amplified by an amplifier 104 and then analog-to-digital converted by an analog-to-digital converter 105, and the result processed in an analyzing unit 110 using the value is displayed on a display unit 109 and is stored in a storage unit 108. A main body control unit 106 is configured to control the light source driving device 103 based on an input of conditions or the like from an input unit 107 or data of the storage unit 108.

In the analyzing unit 110, analysis based on the signal detected by the light detector 102 is executed. Specifically, receiving a digital signal obtained through conversion by the analog-to-digital converter 105, oxygenated hemoglobin change and deoxygenated hemoglobin change are calculated based on the digital signal, for example, by the calculation described in NPL 1.

The probe holder module 21 can be electrically and mechanically bonded to each other by an inter-probe holder relay connector 41, and it is possible to configure a probe holder that covers a plurality of measurement regions.

The present technology can be applied in measurement of optical brain function such as optical topography (OT) or diffuse optical tomography (DOT), an imaging method, and measurement of oxygen saturation degree based on near-infrared spectroscopy.

Example 1

In this example, a probe holder module that can be used for a case where a light source and a detector are modularized will be described. The measurement principle and the overall device configuration are the same as those illustrated in FIG. 1, and a main body of a biological optical measurement device 20 of FIG. 1 is replaced by one or a plurality of light emission modules 32 or a combination of the light detection modules 33.

In FIG. 2, a configuration diagram of a probe holder module having an inter-holder electrical connection connector is illustrated. The probe holder module 21 in the present example includes a joint part 22, the probe insertion hole 23, a part of probe insertion hole 24, a probe connection connector 25, a control unit 27, an electric circuit or electric wiring 28, an inter-holder electrical connection connector 29, and a battery connector 34.

The probe holder module 21 is connected to a battery 26 via a battery cable 34 connecting to the battery connector 34. The light emission module 32 or the light detection module 33 not illustrated is inserted into the probe insertion hole 23 and mechanically coupled. Electrical connection between the light emission module 32 or the light detection module 33 and the probe holder module is performed by the probe connection connector 25, so that electrical power from the battery 25 is supplied.

The probe holder module 21 illustrated in FIG. 2(a) can connect the probe holder module 21 having the same shape vertically and horizontally. By connecting the probe holder module 21, two part of probe insertion holes 24 are combined, and one probe insertion hole 23 can be increased. Accordingly, two probe insertion holes 23 can be increased combined with the added probe insertion hole 23 of the probe holder module 21 for every time when adding one probe holder module 21.

In particular, if the planar shape of the probe holder module 21 is a substantially square shape with a side of 30 mm, by selecting whether to use all the probe insertion holes or every other after connecting the left and right probe holder modules 21, the distance between the probe insertion holes can be set to 30 mm or 15 mm.

These distances are the distances conventionally used in measurement of optical brain function, and the shape of the probe holder module 21 as illustrated in FIG. 2(a) has the effect that it can be easily set to the SD distance of 30 mm or 15 mm.

As illustrated in FIG. 2, in a case where the part of probe insertion hole 24 is used, it is possible to increase a width of the portion having the minimum width on the plan view in a case where the probes are arranged with the same density.

It can be understood by comparing a case where a square module having only the probe insertion hole 23 without the part of probe insertion hole 24 is used and a case where a module having only the part of probe insertion hole 24 without the probe insertion hole 23 in FIG. 2(a), for example. In a case where the probe holders are formed with these modules, the arrangement density of the probe in the lateral direction is the same, but the width of the minimum width portion of the module is different. For example, in a case where one side of the module is defined as m and a diameter of the probe insertion hole is defined as r, the minimum width in the lateral direction is (m−r)/2 in the former case, and is m−r in the latter case. Accordingly, the degree of freedom in designing the circuit and wiring which can be built in the module is greatly expanded. Therefore, using a part of the probe insertion hole is effective for securing a space of a gathered internal circuit.

In addition, a case in which two probe insertion holes are equally formed per 30 mm in the holder is considered. As illustrated in FIG. 2(a), if both the probe insertion hole 23 and the part of probe insertion hole 24 are used, the minimum width in the lateral direction becomes (m−2r)/2 of a region formed at two positions between the probe insertion hole 23 and two parts of probe insertion hole 24. On the other hand, when considering a case where two probe insertion holes 23 are horizontally aligned in a square module without using the part of probe insertion hole 24, the minimum width in the lateral direction becomes (m−2r)/4 of a region formed between the probe insertion hole and the module end surface. That is, since the minimum width is halved, it is also disadvantageous from a viewpoint of mechanical strength. In addition, the width of (m−2r)/2 is secured only at one position between two probe insertion holes.

FIG. 2(b) is an example in which the probe holder module 21 has a substantially square shape with a side of 42 mm and the probe holder module 21 having the same shape is connected to set the distance between the probe insertion holes to 30 mm or 21 mm.

FIGS. 2(c) and 2(d) illustrate the probe holder modules 21 having planar shapes obtained by further dividing FIG. 2(b) into two parts and four parts. The probe holder module 21 obtains a final shape having a higher degree of freedom when forming one probe holder by combining each of the modules and connects the probe ends (side and corner), whereby obtaining the effect of adjusting the final shape.

Although the probe insertion hole 23 is assumed to be circular in here and illustrated, it may be a polygon such as a quadrangle. By setting an inner wall to a flat surface, there is an effect that flat connectors, electrodes, or the like can be arranged. In addition, by setting the shapes of insertion holes of the light emission module 32 and the light detection module 33 different from each other, there is an effect of preventing an insertion error.

In addition, by providing means for electromagnetically or mechanically switching between emission and detection modules, the emission and detection modules may be dynamically switched. For example, in a case where the light emission module 32 and the light detection module 33 are a common module, the module can be used for switching purposes. That is, by using a light emission and detection module including both devices of the light source and the detector, by selecting a device to be operated, by providing a function of replacing the light source and the detector, the probe arrangement can be dynamically changed even if the probe is not mechanically moved. There are effects that there is no need to displace the probe again, the measurement state can be maintained, and the measurement region can be substantially increased.

Here, it is assumed that the probe holder module 21 has a configuration including the joint part 22 without electric wiring and inter-holder electrical connection connector 29. That is, the joint part 22 is configured to only couple mechanically adjacent probe holder modules 21, and the inter-holder electrical connection connectors 29 are electrically connected by being coupled with a cable not illustrated. As another configuration example, the inter-holder electrical connection connector 29 may be eliminated, and the electric wiring may be built in the joint part 22. In addition, in a case where each light emission module 32 and the light detection module 33 connected to the probe holder module 21 have a control unit, there is no need to necessarily have the control unit 27 in the probe holder module 21.

Example 2

FIG. 3 illustrates a configuration having an electric connection terminal built-in joint part 31 instead of the inter-holder electrical connection connector 29 and the joint part 22 in FIG. 2 (a configuration diagram of the probe holder module in which the inter-holder electrical connection connector is built in the joint part). In this manner, it is possible to reduce the area occupied by the parts on the surface of the probe holder module 21 and to reduce the number of mechanical joint parts. Furthermore, by reducing the number of parts, it is effective to reduce the manufacturing cost and the weight.

Furthermore, the probe connection connector 25 may be provided on the inner wall portion of the probe insertion hole 23 and the part of probe insertion hole 24, and the probe itself may serve as an electrical connector. Accordingly, the probe connection connector 25 becomes unnecessary and by reducing the number of the parts, the effect that the area occupied by the parts on the plane of the probe holder module can be reduced and the weight can be reduced is obtained.

In addition, although it is assumed that the battery 26 is arranged outside the probe holder module 21 via a dedicated connector 35, the battery 26 may be built in the probe holder module. By sharing the battery 26 with a plurality of probe holder modules, an effect that there is no need to individually connect each probe holder module to the battery, the number of the battery 26 and the battery cable 34 can be reduced, and the weight and the number of the parts can be reduced is obtained. In addition, a configuration in which the control unit is provided in the probe main body may be adopted and may be a configuration in which the control unit 27 is not provided in the probe holder module 21.

Example 3

Figure 4A:
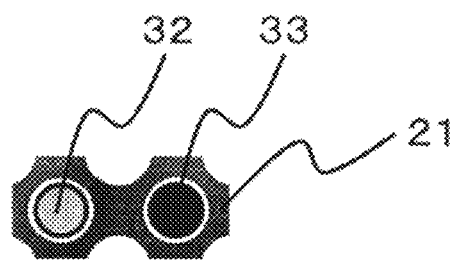
FIGS. 4A and 4B are examples of a plan view illustrating a probe arrangement configuration.
Figure 4B:
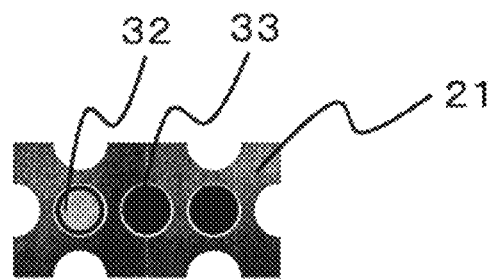

FIG. 4 illustrates a probe arrangement configuration. FIG. 4(a) illustrates a normal arrangement (SD distance of 30 mm) and FIG. 4(b) illustrates a configuration in a case of multidistance arrangement (SD distances of 30 mm and 15 mm).

FIG. 4(a) illustrates a probe arrangement of the probe holder module 21 configured to maintain the light emission module 32 and the light detection module 33 one by one. Even in a case where there is only one measurement point, it is possible to obtain a configuration that does not require excess or deficiency. For example, it can be configured by combining four probe holder modules described in FIG. 3(d).

FIG. 4(b) illustrates a probe arrangement of the probe holder module 21 configured to maintain one light emission module 32 and two light detection modules 33. This is a probe arrangement effective for separating signals from the surface layer and the deep tissue, and, for example, it can be configured by combining two probe holder modules described in FIG. 3(a).

The probe configuration illustrated in FIG. 4 is assumed to be configured by a plurality of probe holder modules 21, but it may be the probe holder module 21 with this configuration as one set. By setting the necessary minimum number of probe holder modules 21 in a set, it is possible to reduce the number of mechanical joint parts, and it is possible to reduce the labor of preparing the probe.

Example 4

Figure 5A:
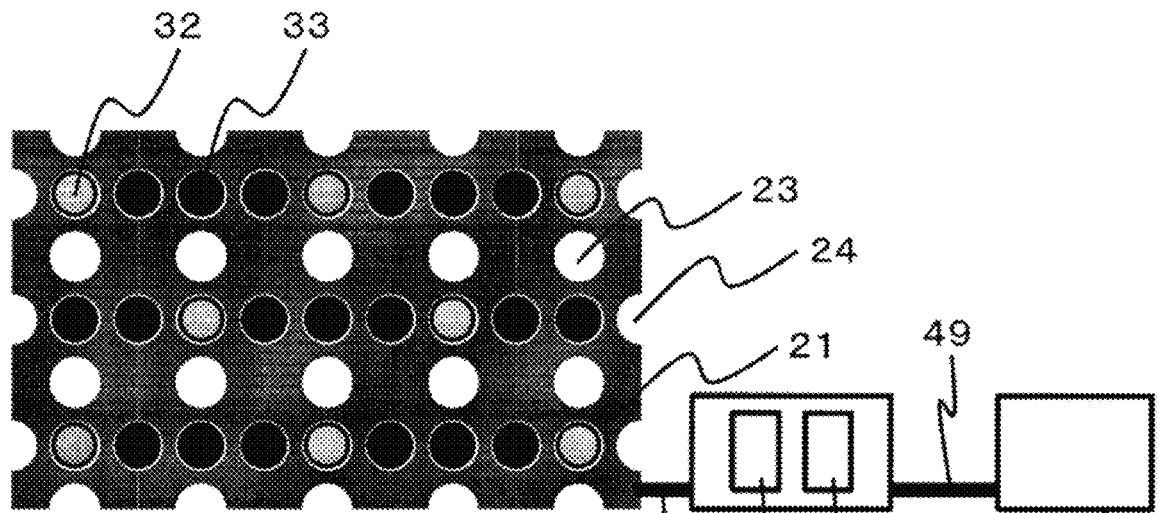
FIGS. 5A to 5C are plan views illustrating a configuration example of the probe holder prepared by combining probe holder modules.
Figure 5B:
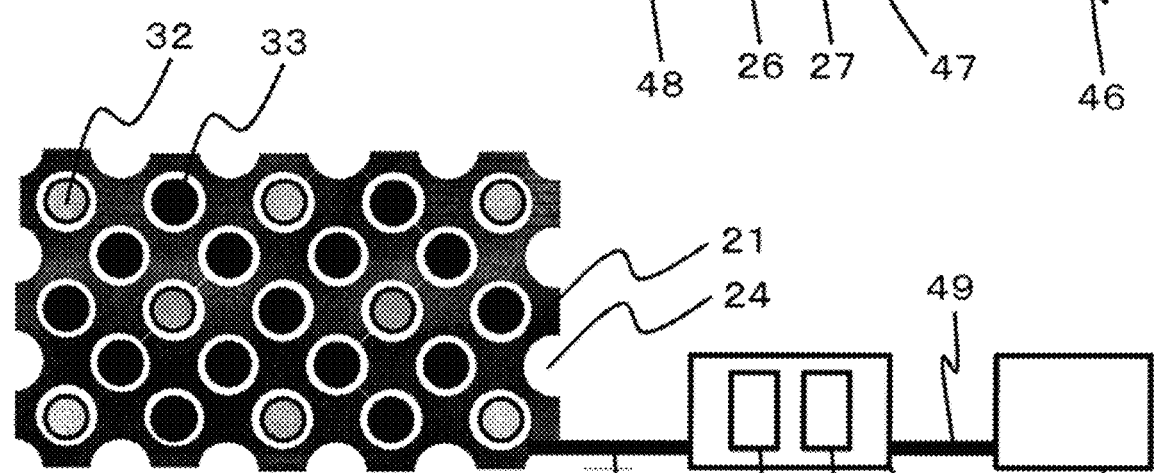
Figure 5C:
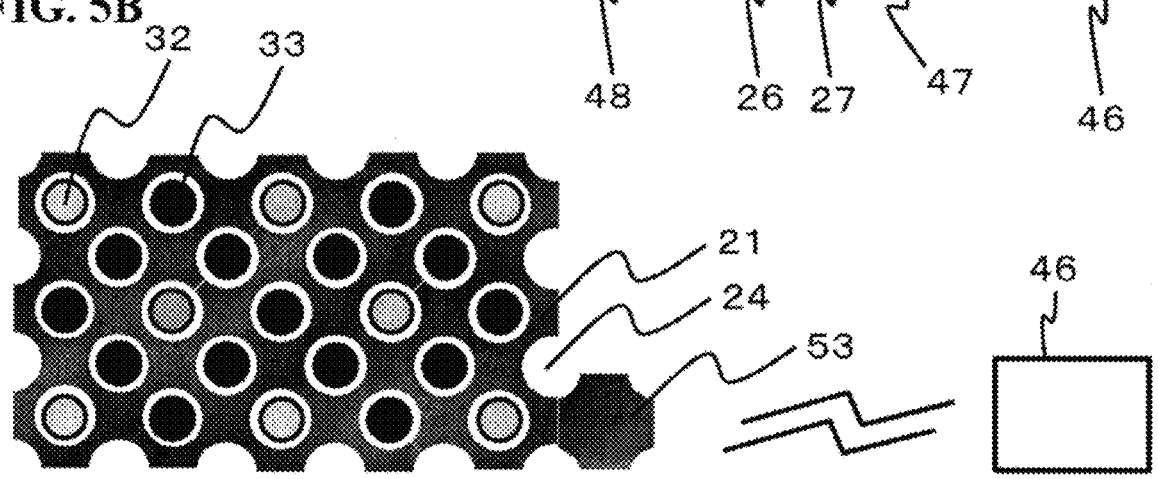

FIG. 5 illustrates a configuration example of a probe holder prepared by combining probe holder modules and aligning in a tile form. FIG. 5(a) illustrates a configuration example of a probe holder corresponding to a double density and 3×5 MD arrangements, FIG. 5(b) illustrates a probe holder configuration example corresponding to the 3×5 MD arrangement (variation), and FIG. 5(c) illustrates a configuration example of a probe holder with a circuit module for performing wireless communication.

FIG. 5(a) is a configuration example of a probe holder corresponding to double density arrangement and 3×5 multidistance arrangement using the probe holder module 21 illustrated in FIG. 2(a) or 3(a).

Figure 3B:
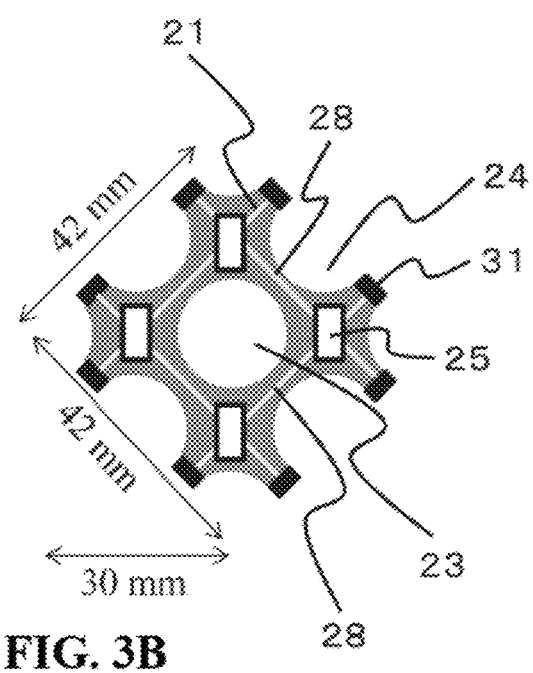
Figure 3C:
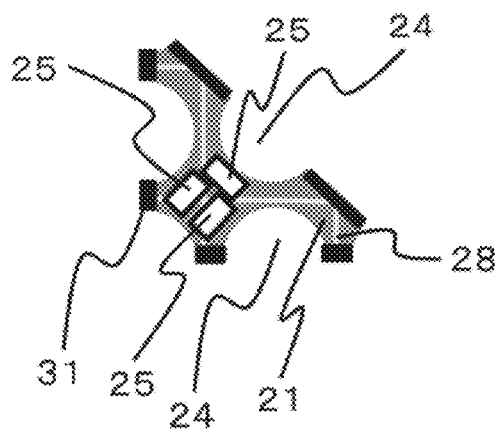
Figure 3D:
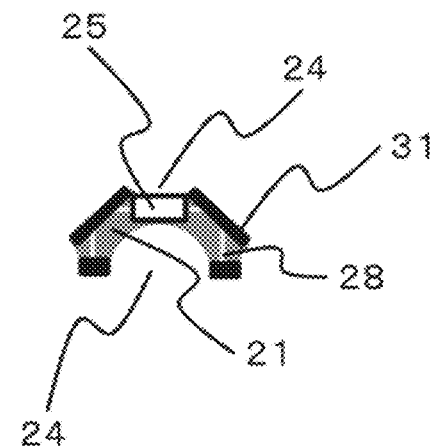

FIG. 5(b) is a configuration example of a probe holder configuration corresponding to the 3×5 multidistance arrangement (variation) mainly using the probe holder module 21 illustrated in FIG. 2(b) or 3(b).

In FIGS. 5(a) and 5(b), an external circuit including the battery 26 and the control unit 27 is stored in a control box 47, and the light emission module 32 and light detection module 33 connected to the probe holder are controlled via a control cable 48. Further, the control box 47 is connected to a personal computer 46 by a communication cable 49 between the control box and the PC. The personal computer 46 has display means of measurement results, setting means of measurement parameters, and input means.

FIG. 5(c) illustrates that the probe holder module 21 illustrated in FIG. 2(b) or 3(b) is mainly used and the control box is connected to the probe holder module 21 as one module (circuit module 53). In this example, a configuration in which the communication cable is connected to the personal computer 46 by wireless communication instead of the communication cable is shown. The circuit module 53 has wireless communication means therein. The light emission module 32 and the light detection module 33 are not arranged in the circuit module 53. The wired communication may be performed without using wireless communication. In addition, it is also possible to disconnect the electric circuit from the circuit module 53 and arrange only the electric wiring so as to make the electrical connection between the modules. Further, only mechanical connection between modules may be performed without the electric circuit or the electric wiring. In this manner, by preparing the modules having various functions having common connection means, the probe holder can be configured according to the situation.

By this configuration, effects that the cable can be eliminated and the weight can be reduced are obtained. In this manner, by using the probe holder expanded with a plurality of probe holder modules 21, a wide range of a brain region can be covered. Since a plurality of probe holder modules 21, the light emission module 32, and the light detection module 33 can be controlled by one control unit 27 at one time, there is no need to have the control unit 27 in each module unit, and it is effective in terms of space and cost. In addition, there is an effect that it is possible to reproduce the conventional multi-channel integrated probe holder (for example).

Example 5

FIG. 6 illustrates a detailed configuration example of the electric connection terminal built-in joint part 31 illustrated in FIG. 3. FIG. 6(a) is a plan view and an elevation view of the probe holder module 21, FIG. 6(b) is a plan view and an elevation view of an inter-probe holder relay connector, and FIG. 6(c) is a plan view and an elevation view of a terminal cover.

The probe holder module 21 is provided with pins including the electric connection terminal built-in joint part 31, a ground (GND) terminal 36, a power supply voltage terminal 37, a clock terminal 38, a communication terminal 39A, and a communication terminal 39B. It is assumed that the pins are accommodated in the outermost shell of the probe holder module 21 in the plan view of the probe holder module 21 in here, but the pins may protrude.

In this example, the inter-probe holder relay connector 41 is used in order to connect the two probe holder modules 21. The inter-probe holder relay connector 41 has a terminal insertion hole 42, and can be inserted to each pin of the ground (GND) terminal 36, the power supply voltage terminal 37, the clock terminal 38, the communication terminal 39A, and the communication terminal 39B of the probe holder module 21. By inserting the inter-probe holder relay connector 41 between the two probe holder modules 21, mechanical and electrical connection can be performed.

A terminal cover 43 is put on the electric connection terminal built-in joint part 31 not connected to the other probe holder module 21 (not used). The terminal cover 43 has the terminal insertion hole 42, and can be inserted into each pin of the ground (GND) terminal 36, the power supply voltage terminal 37, the clock terminal 38, the communication terminal 39A, and the communication terminal 39B of the probe holder module 21. In addition, the terminal cover 43 is configured of an electrically insulating member such as resin or rubber. By the configuration, there is an effect that safe measurement can be performed without contacting the pin of the probe holder module 21 with the subject 10.

The electrical connection can be performed by preparing two types of a probe holder having a pin as an electric connection terminal and a probe holder having a socket without using the inter-probe holder relay connector 41. Although a connection work itself is simplified, there is a disadvantage that the combination of the probe holders is restricted.

Example 6

FIG. 7 illustrates the probe holder module 21 having a curvature. A portion to be in contact with a human of the probe holder module 21 having the probe insertion hole 23 and the part of probe insertion hole 24 and a surface facing the portion are a curved surface portion 52, and the curvature thereof is set to be a value close to the curvature of a human head. In overall probe holder modules described in the above examples, it is possible to have a surface having such a curvature. By the configuration, there are effects that it is easy to fit the shape of the human head and it is easy to wear. In addition, since it is expected that the comfortable fitting is obtained and deviation and floating of the probe holder are reduced, the quality of the signal is improved.

Example 7

FIG. 8 illustrates the probe holder configured by combining the probe holder module 21, the inter-probe holder relay connector 41, and the terminal cover 43. The distance and the angle between the probe holder module 21 can be finely adjusted by forming the inter-probe holder relay connector 41 with an elastic member, for example, whereby the inter-probe holder relay connector 41 is configured to connect the probe holder module 21 to each other without a gap. According to this, there is an effect that it is easy to arrange the module according to the structure such as the curvature of the head surface of the subject 10. Furthermore, the inter-probe holder relay connector 41 has a curvature, and in a case where the planar structure of the probe holder module 21 has a curvature, it may be connected so as to coincide with the curvature of each other.

Example 8

Figure 9A:
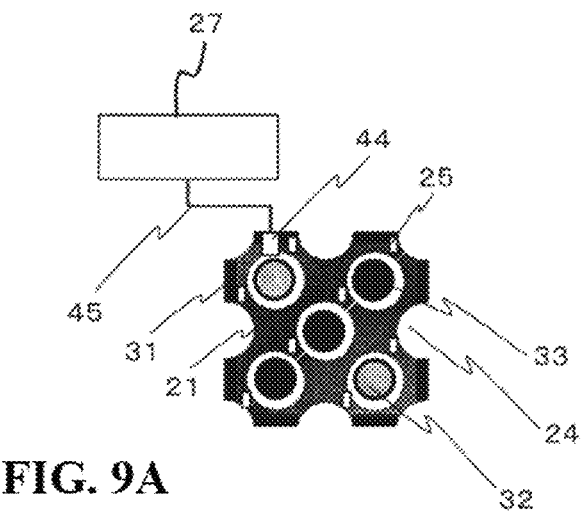
FIGS. 9A to 9C are plan views illustrating a configuration example of the probe holder for controlling 2×2 arrangement units by one control unit.
Figure 9B:
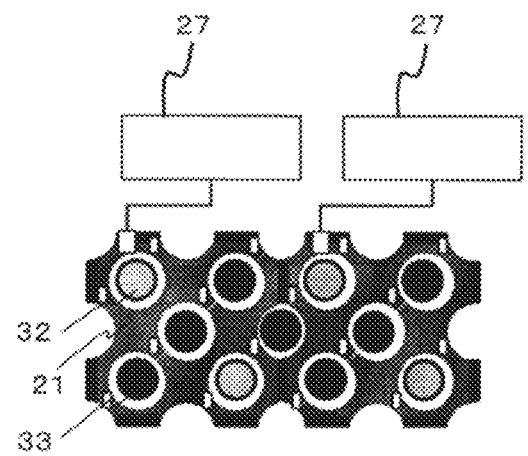
Figure 9C:
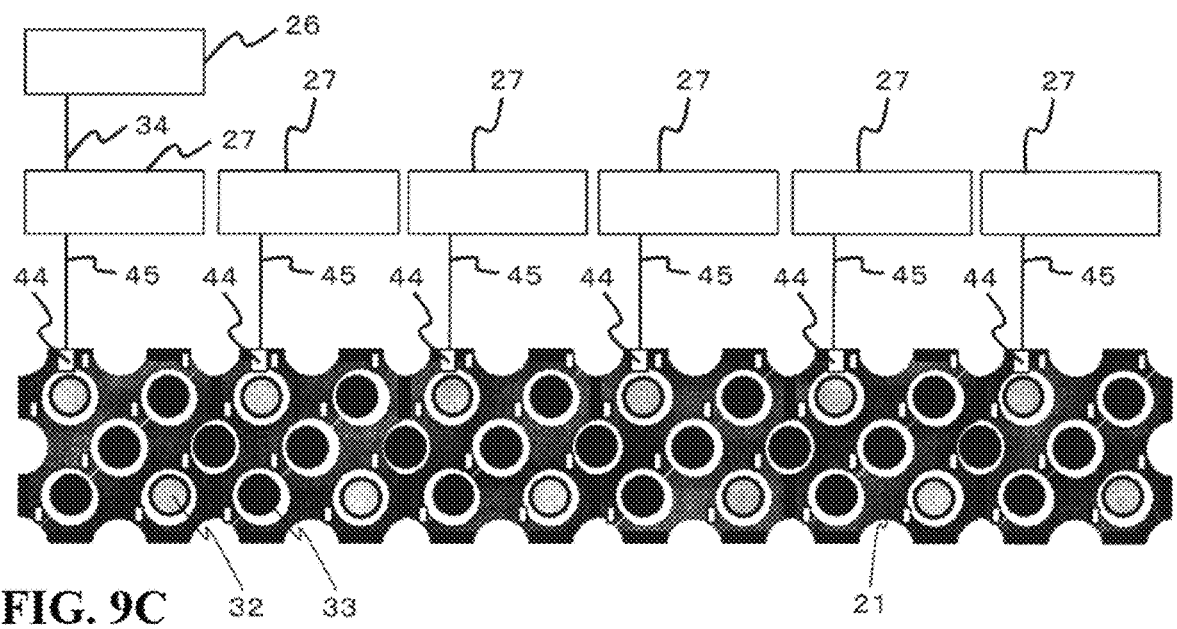

FIG. 9 illustrates a configuration example of the probe holder for controlling 2×2 arrangement units by one control unit. FIG. 9(a) illustrates a 2×2 arrangement, FIG. 9(b) illustrates a 2×4 arrangement, and FIG. 9(c) illustrates a 2×12 arrangement. In each 2×2 arrangement unit, the control unit 27 is provided. The control unit 27 is connected to connection connectors 44 arranged for each 2×2 arrangement units by a connection cable 45. In addition, power is supplied from the battery 26 to the control unit 27 by the battery cable 34.

The control unit 27 may be arranged on the probe holder module 21 or may be built in the electric circuit of the probe holder module 21. Since a configuration in which a small number of the light emission module 32 and the light detection module 33 are controlled by one control unit 27 is effective for lightening processing of each control unit, there is an effect that the measurement point can be easily increased without lowering the measurement performance.

On the other hand, in the configuration in which a lot of the light emission module 32 and the light detection module 33 are controlled by one control unit 27, control becomes simple, program design becomes easy, and wiring can be reduced. Furthermore, in a case where even combination probe arrangements such as 2×2 or 2×4 are adopted, the light emission module 32 and the light detection module 33 may be modularized in a state where the modules are integrated with the probe holder. By the configuration, there is an effect that the light source and the detector can be arranged alternately by directly connecting the holders.

Example 9

Figure 10A:
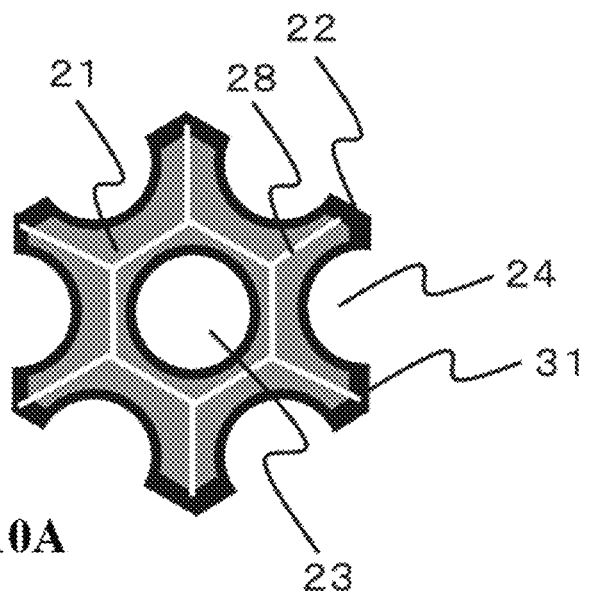
FIGS. 10A and 10B are plan views illustrating a module of a substantially regular hexagonal probe holder module and an example in which modules are configured on a hexagonal lattice arrangement.
Figure 10B:
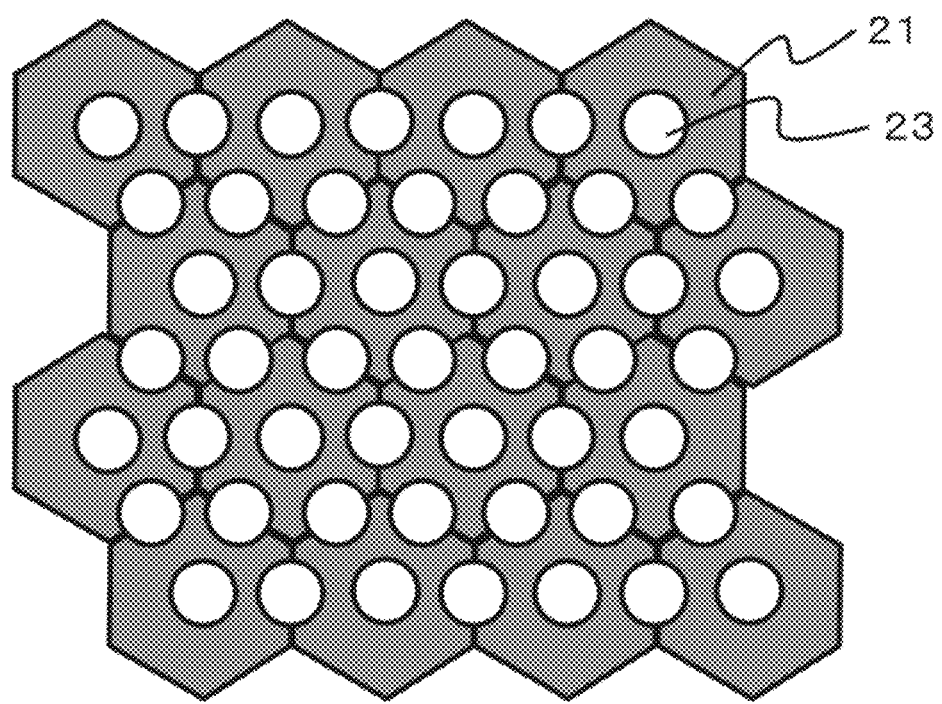

FIG. 10 illustrates the substantially regular hexagonal probe holder module 21. FIG. 10(a) is a plan view of the module 21, and FIG. 10(b) illustrates an example in which the module 21 is arranged in a hexagonal lattice to configure the probe holder.

As illustrated in FIG. 10(a), since each one probe holder module 21 has one probe insertion hole 23 and six probe insertion hole portions 24, the module has substantially four probe insertion holes. Therefore, as illustrated in FIG. 10(b), high density arrangement can be obtained. That is, it is possible to configure many probe insertion holes with a small number of modules.

In addition, as compared with a case where the probe holder having the same density is configured without having such as probe insertion hole part 24, by having such a part of probe insertion hole 24, there is a point that the width of the region having the smallest width in each module planar structure can be made larger. Accordingly, there is an effect that it is advantageous in terms of mechanical strength or mounting a gathered electric circuit.

Furthermore, since there are a large number of connection parts with other modules, some of the connection parts are configured of the joint part 22 without electrical connection, and the remaining connection parts may be configured by electric connection terminal built-in joint part 31. By providing a mechanism for adjusting the distance and angle between the probe holder modules 21 in the joint part 22 or the electric connection terminal built-in joint part 31, even in a case where the probe holder module has a flat plate structure having no curvature, the module can be arranged to fit the curved surface of the human head. Adjustment of the optimum arrangement to the human head shape is effective as the probe holder module 21 is smaller or as many joint parts for adjusting the angle between the modules in the probe holder module 21 are provided.

Example 10

FIG. 11 illustrates a substantially regular octagonal probe holder module. The distances between the light source and the detector are set to 30 mm and 21 mm. A linear part of the joint part is left 8.8 mm and the area of the probe holder can be reduced smaller than that of the square module while maintaining stable joining, there is an effect of weight reduction and reduction of members.

Example 11

FIG. 12 illustrates a substantially square probe holder module. The distances between the light source and the detector are set to 30 mm and 21 mm. Since the linear part of the joint part is 21 mm and the distance between the joint parts is long, there is an effect of stably coupling the probe holder modules 21.

FIG. 13 illustrates a substantially rectangular probe holder module. There is an effect that the circuit accommodating ability is greater by increasing the module area while obtaining the required distance between the light source and the detector. Although the substantially rectangular shape is illustrated, it may have an elliptical shape.

FIG. 14 illustrates a combined arrangement of the substantially regular octagonal probe holder module 21 and a substantially square probe holder module 50. Here, the probe holder module dedicated for short SD distance 50 can be made smaller by reducing the functions. That is, since the necessary circuit size including the connector varies depending on the capacity of the function, the probe holder modules 21 having various sizes according to the necessary circuit size can be combined.

Example 12

FIG. 15 illustrates an example in which the probe holder module 21 is arranged on a human head 10. The probe holder modules 21 are electrically coupled by the electric connection terminal built-in joint part 31. The electric connection terminal built-in joint part 31 includes at least a communication line, a clock line, a power supply, and a GND line. The light emission module 32 and the light detection module 33 are connected to the probe insertion hole 23. Furthermore, it is connected to the control box 47 having at least the battery 26 and the control unit 27, and wireless communication means 51, it is possible to perform measurement in this configuration, and data can be transmitted to the personal computer 46 not shown.

This configuration is effective for fixing a relative positional relationship between the probe holders. It is possible to easily connect the conventionally used probe arrangements (4×4, 3×5, 3×11, or the like). There is an effect that it is easy to match the clock between the probe holder modules.

FIG. 16 illustrates an example in which the probe holder module 21 is arranged on the human head 10 so as to forma probe insertion hole. A part of the probe insertion hole is formed on the side of the probe holder module 21. By combining a part of the probe insertion hole, a new probe insertion hole 23 is formed, and it is possible to configure a lot of the probe insertion holes 23 than the total number of probe insertion holes of each probe holder module 21. This configuration is effective for a seamless wide range cover. In addition, it is effective in reducing the electric circuit space. Even in a case where the conventional arrangements (3×3, 3×5, 4×4, 2×8, 3×11, or the like) is modularized, there is an effect that seamless expansion is possible.

Example 13

FIG. 17 illustrates a probe arrangement design screen. An arbitrary probe arrangement can be obtained by combining various types of probe holder modules using the probe holder module 21, the light emission module 32, and the light detection module 33 of the above-described examples.

FIG. 17 is a tool design screen for allowing the user to freely design its arrangement in the device obtained by the present example. As the parameter setting, input means of a setting value 54 of the number of light sources, a setting value 55 of the number of light detectors, a setting value 56 of the minimum. SD distance (the distance between the light source and the light detector), and a setting value 57 of a the maximum SD distance (the distance between the light source and the light detector) is provided. The number of the light emission position 12 and the light detection position 13 in a probe arrangement setting screen and input means 60 is changed according to the input. The user can freely set the arrangements of the light emission position 12 and the light detection position 13 in the probe arrangement setting screen and the input means 60.

Thereafter, after pressing a calculation button 61 by the user, a combination of the SD distances of a setting value 56 or more of the preset minimum SD distance (distance between the light source and the light detector) and a setting value 57 or less of the preset maximum SD distance (distance between the light source and the light detector) is calculated, one or a plurality of SD distances are displayed as a result of calculation of an effective SD distance 58, and furthermore, the number of measurement points corresponding to each calculated SD distance is displayed as a result of calculation of the number of measurement points in each effective SD distance 59.

By this configuration, it is possible for the user to easily implement the design of the free arrangement, and there are effects that it is possible to optimize the signal detection method depending on the probe arrangement (for example, a continuous lock-in method, a time division method, a time division lock-in method, a spread spectrum modulation method, or the like), and it is possible to optimize the parameters in each method.

With reference to the information obtained on this screen, the user can combine, add, or delete various probe holder modules. In addition, the information set on this screen can be set in the probe holder module 21 by a software including communication means with each module which is not illustrated, means for reading setting values of each module, and a processing unit for sending setting values to the control unit of each module.

FIG. 18 is a diagram illustrating a flow chart when setting the probe arrangement. In the same drawing, the number of light sources and detectors to be used is set (Step S181). The minimum and maximum distances between the light source and the detector is set by manual input or the like (Step S182). The light sources and the detectors of the set number of the light sources and the detectors are displayed on a screen (Step S183). A position of each of the light source and the detector is set by manual input (manual set by a mouse or the like) (Step S184). A distance between each of the light sources and a pair of detectors is calculated and the number of measurement points corresponding to each of the SD distances is calculated and displayed (Step S185). Information on set pair of the light source and the detector is transferred to the probe holder module 21, the light emission module 32, or the light detection module 33 (Step S186). The setting result is stored (Step S187).

The control method after configuring the probe holder by combining the probe holder module once and inserting the probe is the same as that of the conventional probe holder. For example, the technology of PTL 1 can be applied to the probe calibration method or the like.

According to the above-described examples, a stable and easy extension of the probe holder and the free probe arrangement in the biological optical measurement device can be obtained. Easy replacement and maintenance of the probe module (light source and detector module) can be obtained. Furthermore, it is possible to use only the necessary minimum number of probes, and it is possible to obtain an apparatus with space saving and low cost.

Note that the present invention is not limited to the embodiments explained above. Various modifications are included in the present invention. For example, a part of the configuration of a certain example can be replaced with the configuration of another example. In addition, the configuration of another example can also be added to the configuration of a certain example. In addition, the configuration of another example can be added to, deleted from, and replaced with a part of the configurations of the examples.

INDUSTRIAL APPLICABILITY

The present invention can be used for various types of optical measurement devices using light, particularly visible light or near-infrared light.

REFERENCE SIGNS LIST

10: subject
12: light emission position

13: light detection position
14: light detection position
20: main body of a biological optical measurement device
21: probe holder module
22: joint part
23: probe insertion hole
24: a part of probe insertion hole
25: probe connection connector
26: battery
27: control unit
28: electric circuit or electric wiring
29: inter-holder electrical connection connector
30: light
31: electric connection terminal built-in joint part
32: light emission module
33: light detection module
34: battery cable
35: battery connector
36: ground (GND) terminal
37: power supply voltage terminal
38: clock terminal
39A: terminal for communication
39B: terminal for communication
40: optical waveguide
41: inter-probe holder relay connector
42: terminal insertion hole
43: terminal cover
44: control unit and connection connector
45: control unit and connection cable
46: personal computer
47: control box
48: control cable
49: communication cable between control box and PC
50: probe holder module dedicated for short SD distance
51: wireless communication means
52: curved surface portion
53: circuit module
54: setting value of the number light sources
55: setting value of the number of light detector
56: setting value of minimum SD distance (distance between light source and light detector)
57: setting value of maximum SD distance (distance between light source and light detector)
58: result of calculation of effective SD distance
59: calculation result of the number of measurement points in each effective SD distance
60: probe arrangement setting screen and input means
61: calculation button
101: light source
102: light detector
103: light source driving device
104: amplifier
105: analog-to-digital convertor
106: main body control unit
107: input unit
108: storage unit
109: display unit
110: analysis unit

The invention claimed is:

1. A probe holder comprising:
a plurality probe holder modules configured to be a part of the probe holder for an optical measurement;
a light emission probe and a light detection probe;
wherein the probe holder is mountable on an object to be measured,
wherein each of the plurality of probe holder modules includes:
a first holding part that, by itself, mechanically holds one of the light emission probe and the light detection probe;
a second holding part that is configured to be in contact with only a portion of a circumference of another one of the light emission probe and the light detection probe, and, in cooperation with another one of the plurality of probe holder modules that is configured to be in contact with only an opposite portion of the circumference of the another one of the light emission probe and the light detection probe, to mechanically hold the another one of the light emission probe and the light detection probe;
at least one of an electric circuit and electric wiring that is electrically connectable to at least one of the light emission probe and the light detection probe;
a terminal through which the at least one of the light emission probe and the light detection probe is electrically connectable to the at least one of the electric circuit and the electric wiring;
a mechanical connection part that is mechanically connectable between two of the plurality of probe holder modules; and
an electrical connection part that is electrically connectable between the two of the plurality of probe holder modules.

2. The probe holder according to claim 1,
wherein, in the second holding part,
a part of a side surface of each of the plurality of probe holder modules forms only a part of an insertion hole into which at least one of the light emission probe and the light detection probe is inserted, and
the part of the insertion hole is configured to mechanically hold at least one of the light emission probe and the light detection probe in cooperation with a part of another one of the plurality of probe holder modules.

3. The probe holder according to claim 2,
wherein an internal insertion hole, which is formed inside the side surface of each of the plurality of probe holder modules and mechanically holds at least one of the light emission probe and the light detection probe, is provided as the first holding part.

4. The probe holder according to claim 1,
wherein each of the plurality of probe holder modules has a flat plate shape.

5. The probe holder according to claim 1,
wherein the mechanical connection part and electrical connection part are configured to perform mechanical connection and electrical connection by inserting an inter-probe holder relay connector that is a separate member between the two of the plurality of probe holder modules.

6. A biological optical measurement probe holder module comprising:
a connector that is electrically connectable to at least one of a light emission probe and a light detection probe;
at least one of an electric circuit and electric wiring;
a joint part that is joinable to another biological optical measurement probe holder module;
an electrical connection part that is electrically connectable to the another biological optical measurement probe holder module;
a first probe insertion hole disposed in a central portion of the biological optical measurement probe holder module; and
a plurality of partial probe insertion holes disposed around an outermost periphery of the biological optical measurement probe holder module, each of the partial probe insertion holes including only half of a circumference of a hole.

7. The biological optical measurement probe holder module according to claim 6, further comprising:
a probe insertion hole side surface that coincides with a part of a side surface shape of at least one of the light emission probe and the light detection probe.

8. The biological optical measurement probe holder module according to claim 6,
wherein the electrical connection part is built in the joint part.

9. The biological optical measurement probe holder module according to claim 6,
wherein the joint part is capable of adjusting at least one of a distance between the biological optical measurement probe holder module and the another biological optical measurement probe holder module and a connection angle.

10. The biological optical measurement probe holder module according to claim 6,
wherein the biological optical measurement probe holder module has a function of electromagnetically or mechanically switching a light emission probe or a light detection probe as a probe to be inserted, and
wherein an arrangement of the light emission probe or the light detection probe can be changed.

11. A method for configuring an optical measurement probe holder, the method comprising:
preparing a plurality of probe holder modules, each of which includes
a first holding part that, by itself, mechanically holds at least one of a light emission probe and a light detection probe,
a second holding part that is configured to be in contact with only a portion of a circumference of another one of the light emission probe and the light detection probe, and, in cooperation with another one of the plurality of probe holder modules that is configured to be in contact with only an opposite portion of the circumference of the another one of the light emission probe and the light detection probe, to mechanically hold the another one of the light emission probe and the light detection probe,
at least one of an electric circuit and electric wiring that is electrically connectable to at least one of the light emission probe and the light detection probe,
a terminal through which the at least one of the light emission probe and the light detection probe is electrically connectable to the at least one of the electric circuit and the electric wiring,
a mechanical connection part that is mechanically connectable between two of the plurality of probe holder modules, and
an electrical connection part that is electrically connectable between the two of the plurality of probe holder modules; and
coupling the plurality of probe holder modules together by the mechanical connection part and the electrical connection part of each of the plurality of probe holder modules.

12. The method for configuring a probe holder according to claim 11,
wherein, in the holding part,
a part of a side surface of each of the plurality of probe holder modules forms a part of an insertion hole into which at least one of the light emission probe and the light detection probe is inserted, and
a part of the insertion hole is configured to mechanically hold at least one of the light emission probe and the light detection probe in cooperation with another one of the plurality of probe holder modules.

13. The method for configuring a probe holder according to claim 11,
wherein the plurality of probe holder modules includes a plurality of types of probe holder modules having different shapes.

14. The method for configuring a probe holder according to claim 11,
wherein the plurality of probe holder modules includes a connection dedicated probe holder module to which neither the light emission probe nor the light detection probe is connected, and
wherein the connection dedicated probe holder module includes
a mechanical connection part that is mechanically connected to another one of the plurality of probe holder modules, and
an electrical connection part that is electrically connected to the another one of the plurality of probe holder modules.

15. The probe holder according to claim 1,
wherein each of the probe holder modules has a curved surface.

* * * * *